(12) United States Patent
Watson

(10) Patent No.: US 12,065,857 B2
(45) Date of Patent: Aug. 20, 2024

(54) FACILITATION OF OPENING AND CLOSING OF STRUCTURES WITHOUT USE OF HAND

(71) Applicant: Amin, Turocy & Watson, LLP, Beachwood, OH (US)

(72) Inventor: Thomas Edward Watson, Mercer Island, WA (US)

(73) Assignee: Amin, Turocy & Watson, LLP, Beachwood, OH (US)

( * ) Notice: Subject to any disclaimer, the term of this patent is extended or adjusted under 35 U.S.C. 154(b) by 958 days.

(21) Appl. No.: 17/026,019

(22) Filed: Sep. 18, 2020

(65) Prior Publication Data

US 2021/0381274 A1   Dec. 9, 2021

Related U.S. Application Data

(60) Provisional application No. 63/034,280, filed on Jun. 3, 2020.

(51) Int. Cl.
 *E05B 1/00* (2006.01)
 *A61L 2/00* (2006.01)
 (Continued)

(52) U.S. Cl.
 CPC .......... *E05B 1/0069* (2013.01); *A61L 2/0047* (2013.01); *E05B 1/0053* (2013.01); *E05B 7/00* (2013.01); *E05B 47/0038* (2013.01)

(58) Field of Classification Search
 CPC ........ E05B 1/0069; E05B 1/0053; E05B 7/00; E05B 47/0038; A61L 2/0047
 See application file for complete search history.

(56) References Cited

U.S. PATENT DOCUMENTS

| 6,189,183 B1* | 2/2001 | Hartselle, III | ........ E05B 1/0069 16/412 |
|---|---|---|---|
| 7,810,215 B2* | 10/2010 | Houis | .................. E05B 1/0015 16/412 |

(Continued)

FOREIGN PATENT DOCUMENTS

| FR | 2873423 A1 * | 1/2006 | ........... A47K 13/105 |
|---|---|---|---|
| WO | WO-2021205021 A1 * | 10/2021 | ........... E05B 1/0053 |

OTHER PUBLICATIONS

"The Safe Way to Avoid Contaminated Surfaces—CleanKey + Carabiner" KeySmart [https://www.getkeysmart.com/products/cleankey], retrieved Dec. 18, 2020, 6 pages.

*Primary Examiner* — Christine M Mills
*Assistant Examiner* — Matthew J Sullivan
(74) *Attorney, Agent, or Firm* — Amin, Turocy & Watson, LLP

(57) ABSTRACT

Opening and closing a door without the use of one's hands is facilitated. For instance, an apparatus can comprise one or two rotatable rings. For a one ring apparatus, the ring can have an opening so that the inner cross section of the opening of the ring can be pushed with a forearm or knee so that the ring will rotate and the person can then pull on the ring with his/her forearm or knee to open the door. In a two-ring apparatus, two adjacent rings, both with openings, can comprise similar push surfaces. When pushed on the pushed surfaces, the rings will rotate and the cross sections of the openings of the rings come into contact with one another, creating a surface against which a forearm or knee can pull on to open the door. A rotation plane converter can turn a doorknob using the apparatus.

13 Claims, 15 Drawing Sheets

(51) Int. Cl.
    *E05B 7/00*         (2006.01)
    *E05B 47/00*      (2006.01)

(56) References Cited

U.S. PATENT DOCUMENTS

| | | | | |
|---|---|---|---|---|
| 8,522,482 | B2 * | 9/2013 | Buck | E05B 1/0069 |
| | | | | 49/386 |
| 11,060,322 | B2 * | 7/2021 | Lin | E05C 19/10 |
| 11,524,085 | B2 * | 12/2022 | Schumacher | G01P 13/00 |
| 2014/0000170 | A1 * | 1/2014 | Buck | E05B 1/0053 |
| | | | | 49/353 |
| 2014/0137369 | A1 * | 5/2014 | Street | E05B 1/0069 |
| | | | | 16/111.1 |
| 2014/0208541 | A1 * | 7/2014 | Cowburn | B25G 1/00 |
| | | | | 16/110.1 |
| 2022/0010593 | A1 * | 1/2022 | McDaniel | E05F 11/54 |
| 2022/0307286 | A1 * | 9/2022 | Hagiwara | E05B 65/0035 |
| 2022/0333404 | A1 * | 10/2022 | McIntire | E05B 1/0069 |
| 2023/0302174 | A1 * | 9/2023 | Taghipour | A61L 2/10 |
| | | | | 250/454.11 |
| 2023/0332432 | A1 * | 10/2023 | Lee | E05B 7/00 |

\* cited by examiner

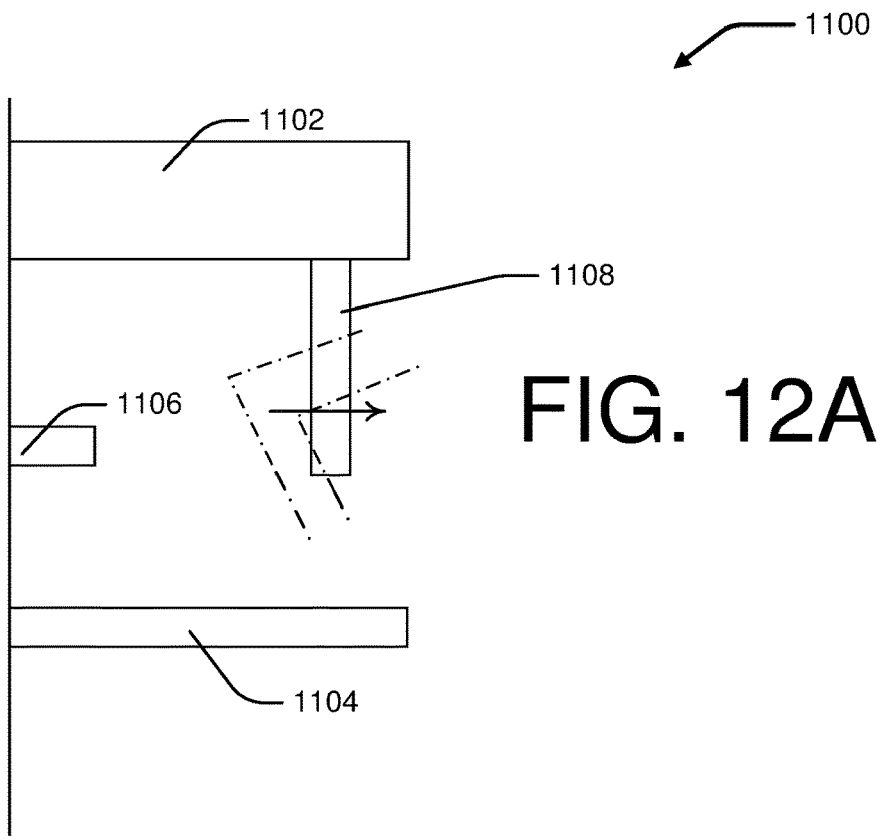
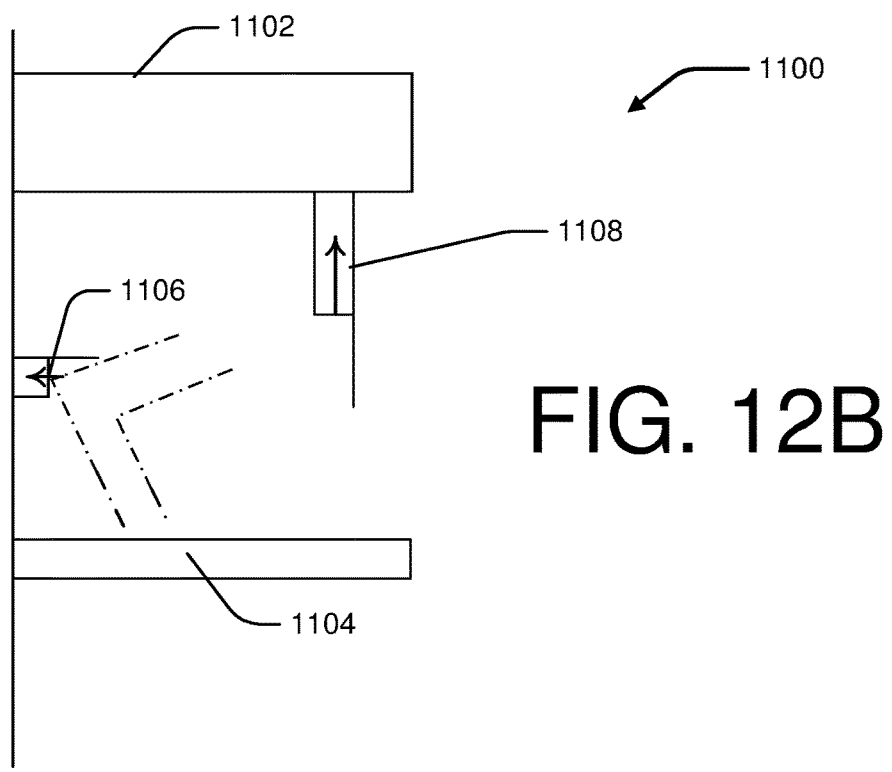

FACILITATION OF OPENING AND CLOSING OF STRUCTURES WITHOUT USE OF HAND

RELATED APPLICATION

The subject patent application claims priority to U.S. Provisional Patent Application No. 63/034,280, filed Jun. 3, 2020, and entitled "FACILITATION OF OPENING AND CLOSING OF STRUCTURES WITHOUT USE OF HAND," the entirety of which application is hereby incorporated by reference herein.

TECHNICAL FIELD

The subject patent application relates to facilitating the opening and/or closing of structures, such as doors, cabinets, etc., by a user without involving touching the structure by the user's hand, for a sanitary disconnect between the user's hand and the structures.

BACKGROUND

Some pathogens, including viruses, can live on surfaces for some period. Surfaces that come into contact with many different people can contribute to the spread of disease from person to person. Doorknobs, door handles, and other structure-opening mechanisms commonly come into contact with many different peoples' hands. It may be desirable to be able to open a door or other structure without the use of one's hands and without having to replace the door, doorknob, or other structure-opening mechanism.

People often touch their eyes, nose, and mouth with their hands. Therefore, an infected person might carry the disease-causing pathogen on his/her hands. An uninfected person might become infected if his/her hands come into contact with a surface containing the pathogen. Due to usual lack of contact between one's face and one's forearm, knee, or foot, door opening mechanisms that only come into contact with one's forearm, knee, or foot, as opposed to a hand, may be desirable.

The above-described background relating to conventional structure-opening mechanisms is intended to provide a contextual overview of some current issues, and is not intended to be exhaustive. Other contextual information may become further apparent upon review of the following detailed description.

BRIEF DESCRIPTION OF THE DRAWINGS

The technology described herein is illustrated by way of example and not limited in the accompanying figures in which like reference numerals indicate similar elements and in which:

FIG. 12A illustrates an example diagram of a structure-opening apparatus comprising a lowering/rising vertical bar in the lowered position.

FIG. 12B illustrates an example diagram of a structure-opening apparatus where an elbow is pushing in the horizontal pushing bar to a second push point to raise the vertical bar.

DETAILED DESCRIPTION

Figure 1:
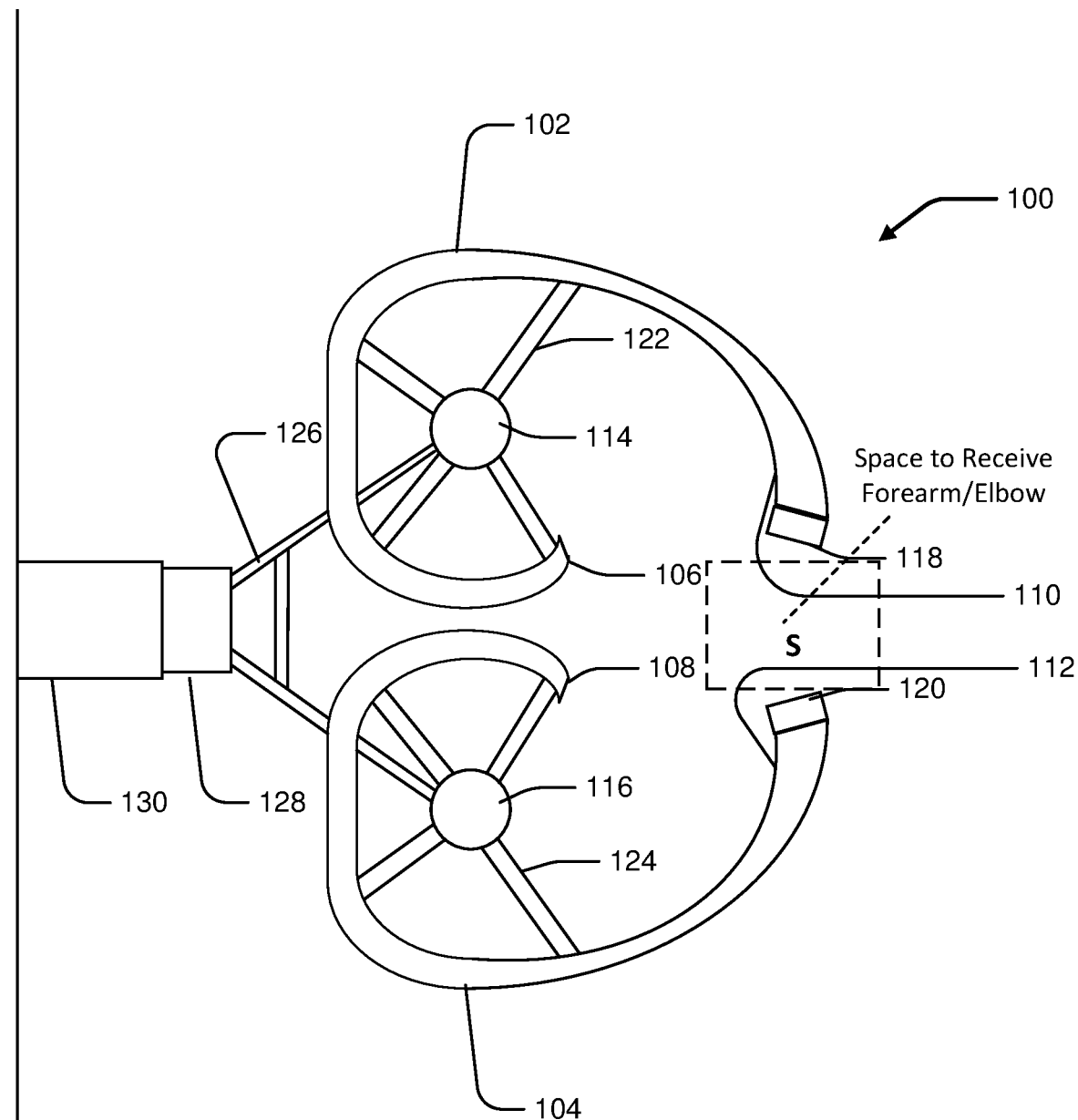
FIG. 1 illustrates an example of a two-ring structure-opening apparatus in the open position.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

In addition, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Various aspects or features will be presented in terms of systems that may include a number of devices, components, modules, and the like. It is to be understood and appreciated that the various systems may include additional devices, components, modules, etc. and/or may not include all of the devices, components, modules etc. discussed in connection with the figures. A combination of these approaches also can be used.

Embodiments of the structure-opening apparatuses described herein comprise door attachment hardware that can attach to some type of conventional door, doorknob, door handle, or other structure. Embodiments of the structure-opening apparatuses are configured to enable a person to open a door or other structure without the use of his/her hand. The ability to open a door or other structure without using one's hands may be desirable to impede the spread of pathogens from person to person.

Further, air flow across a surface can be used to facilitate evaporation of any life sustaining fluids within the air flow. This could facilitate the removal of pathogens from a surface. Additionally, ultraviolet radiation and/or heat can be used to disinfect surfaces. It may be desirable to subject commonly touched surfaces to air flow and ultraviolet radiation.

One or more of the embodiments described herein relate to a hands-free door-opening apparatus comprising one ring. The use of the term 'ring' herein is meant to cover any at least partially enclosed annular element, enabling insertion of a forearm or elbow therein without contact with the user's hand. In one non-limiting example, the one-ring apparatus comprises a rotatable ring that is unenclosed, a supporting frame, and a door attachment hardware. As described further below, a person's forearm, elbow (or knee) can push on the cross section of the first rotatable ring so that the rotatable ring rotates. When the rotatable ring rotates, the unenclosed portion of the rotatable ring is directed downwards (useful for opening or closing) or upwards (useful for placing forearm/elbow in or removing forearm/elbow therefrom). The person can stop pushing on the cross section and the rotatable ring will temporarily hold its rotated position, or stay in an extended rotated position until urged away from the extended rotated position. Then, using the forearm or knee, the person can pull perpendicularly to the door so that the rotatable ring catches the forearm or knee, and a force is thereby exerted against the rotatable ring that causes the door to open or close depending on the configuration of the door, and its current position.

An example, two-ring apparatus functions similarly except that the first rotatable ring and a second rotatable ring, which are both unenclosed in the example, can work in concert, and are positioned so that one cross section of each ring can be pushed by a forearm or knee with a single motion and the rings will rotate so that the other two cross sections (one on each ring) will meet and latch together. A user can then pull on the two rings near the latched cross sections to pull the door open.

In one or more embodiments, a rotation plane converter could be utilized as part of the one-ring apparatus or the two-ring apparatus so that the pushing force applied to the rotatable ring(s) is translated into rotational force to turn a doorknob or door handle.

In one or more embodiments, a structure-opening apparatus comprises a rotatable ring configured to rotate about an axis that is perpendicular to a surface of a door. The rotatable ring can be pushed using a forearm or knee so that the ring rotates about an axis that is perpendicular to the surface of a door.

In one or more embodiments, a structure-opening apparatus can comprise two gripping elements configured to move towards each other when a motion sensor detects the presence of an object between the gripping elements. The gripping elements can grip an arm, leg, or foot so that a person could pull a door open without the use of his/her hands.

In one or more embodiments, a structure-opening apparatus can comprise a housing element, a horizontal push bar, and a vertical pull bar. A person can use his/her forearm or elbow to push the horizontal push bar to a first push point that lowers/closes the vertical pull bar so that the person can apply a pulling force perpendicular to the door. A person can use his/her forearm or elbow to push the horizontal push bar to a second push point to retract the vertical pull bar.

In one or more embodiments, an ultraviolet light can be used to direct ultraviolet radiation at any surface on the structure-opening apparatus that comes into contact with an arm, leg or foot to disinfect the surface after it is used. A wind producing element could direct air flow at any surface on the structure-opening apparatus that comes into contact with an arm, leg, or foot to facilitate evaporation of life sustaining fluids.

FIG. 1 illustrates an example, non-limiting apparatus 100 in an open position, in which a forearm can easily be received for an opening or closing experience with respect to a door, cabinet, closet, etc. Apparatus 100 comprises a first rotatable ring 102, a second rotatable ring 104, a first forearm push point 106, a second forearm push point 108, a first pulling element 110, a second pulling element 112, a first ring rotation element 114, a second ring rotation element 116, a first latching element 118, a second latching element 120, first spokes 122, second spokes 124, a supporting frame 126, a door attachment hardware element 128, and a door knob/handle 130. For the avoidance of doubt, the particular shapes, sizes, widths, lengths, curvature, etc. of the various elements of FIG. 1 can be varied, consistent with their structural purposes and functions as described herein. In addition, the scale and relative positions of elements can be varied where achieving a same or similar opening and closing of the door without using a hand.

In regards to this example apparatus 100, optional details include the following. The supporting frame 126 holds the first rotatable ring 102 and the second rotatable ring 104 so they are positioned vertically and the first rotatable ring 102 is directly above the second rotatable ring 104. Both the first rotatable ring 102 and the second rotatable ring 104 are unenclosed. The inner cross section of the first rotatable ring 102 is directly above the inner cross section of the second rotatable ring 104. The first forearm push point 106 is located on the inner cross section of the first rotatable ring 102 and the second forearm push point 108 is located on the inner cross section of the second rotatable ring 104. The first latching element 118 is located on the outer cross section of the first rotatable ring 102 and the second latching element 120 is located on the outer cross section of the second rotatable ring 104. The first pulling element 110 is located on the first rotatable ring 102 adjacent to the first latching element 118 and the second pulling element is located on the second rotatable ring 104 adjacent to the second latching element 120. The first ring rotation element 114 is located at the center of the first rotatable ring 102 and the second ring rotation element 116 is located at the center of the second rotatable ring 104. The first ring rotation element 114 is connected to the first rotatable ring 102 by the first spokes 122 and the second ring rotation element 116 is connected to the second rotatable ring 104 by the second spokes 124. The supporting frame 126 supports the first and second rotatable rings 102, 104, and the door attachment element 128 attaches apparatus 100 to a door (e.g., the vertical line to the left of FIG. 2), doorknob 130, door handle, or other structure.

Figure 2:
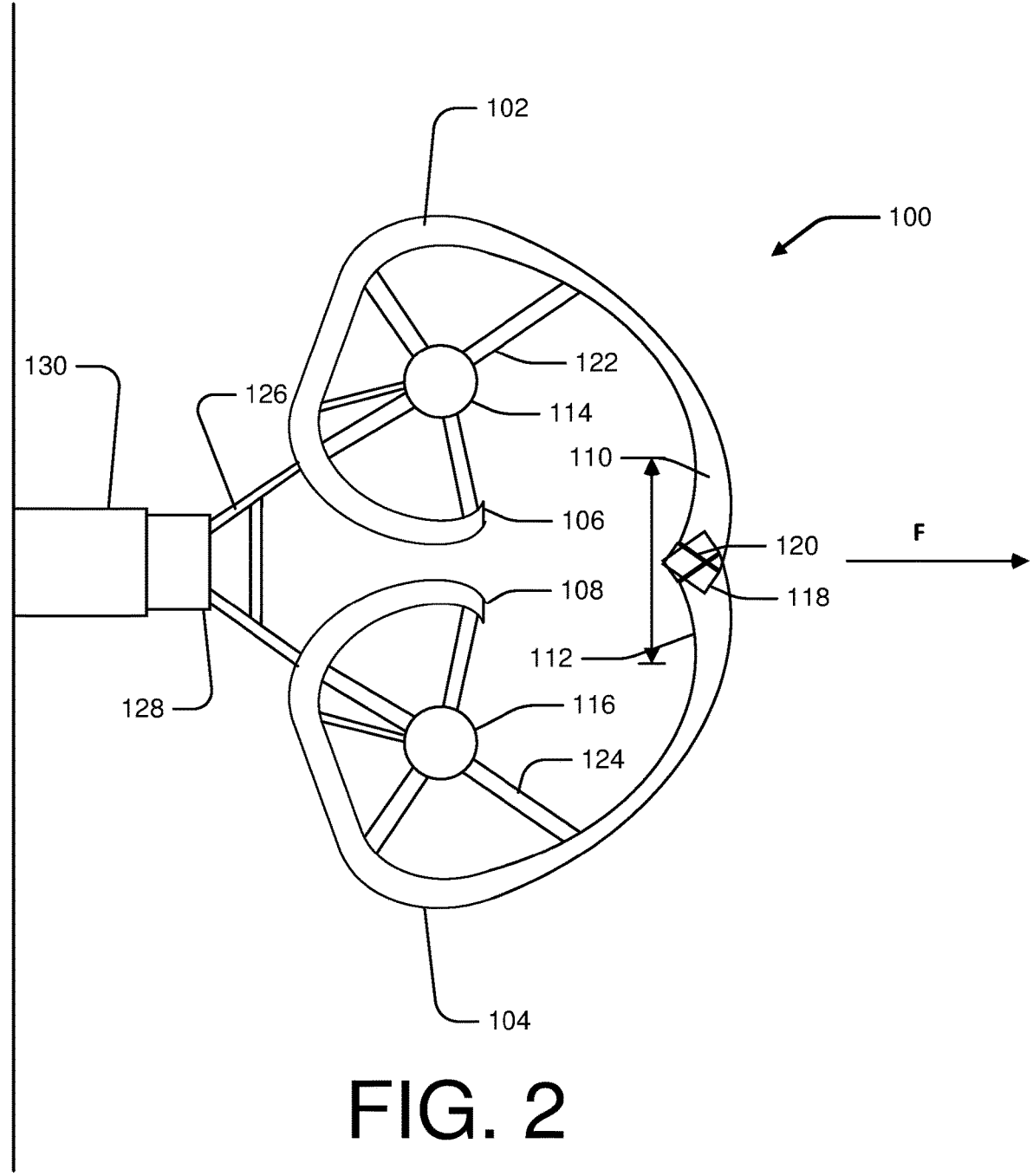
FIG. 2 illustrates an example diagram of a two-ring structure-opening apparatus in the closed position.

In an embodiment, in the open position, a user's forearm or elbow can be received freely via a space S between the first latching element 118 and the second latching element 120, using a motion towards the door, and by continuing the motion of the user's forearm or elbow towards the door, the user's forearm or elbow engages the first forearm push point 106 and/or the second forearm push point 108 causing the rotation of the first rotatable ring 102 and the second rotatable ring 104 such that the first latching element 118 and the second latching element 120 engage one another, and couple according to a magnetic force, a latching force of matable geometries, etc., causing the apparatus 100 to be in the closed position of FIG. 2.

As noted, FIG. 2 illustrates apparatus 100 in the closed position. In this regard, FIG. 2 also illustrates the first rotatable ring 102, the second rotatable ring 104, the first forearm push point 106, the second forearm push point 108, the first pulling element 110, the second pulling element 112, the first ring rotation element 114, the second ring rotation element 116, the first latching element 118, the second latching element 120, the first spokes 122, the second spokes 124, the supporting frame 126, the door attachment hardware element 128, and the door knob/handle 130. In the closed position of apparatus 100, the user's forearm can be used to pull against the first pulling element 110, and/or the second pulling element 112, and/or nearby parts of the first rotatable ring 102 and the second rotatable ring 104, in order to effectuate a force F indicated by vector/arrow labeled F against the first pulling element 110, and/or the second pulling element 112, and/or nearby parts of the first rotatable ring 102 and the second rotatable ring 104, which force F can open or close a door, or other structure.

In an example embodiment, when in the closed position, in order to return to the open position, a user's forearm or elbow can push the first forearm push point 106 and/or the second forearm push point 108, using a motion towards the door opposite force F, causing the rotation of the first rotatable ring 102 and the second rotatable ring 104 back towards the open position of FIG. 1. As the first rotatable ring 102 and the second rotatable ring 104 begin to rotate back to the open position, the first latching element 118 and the second latching element 120 move away from each other until they de-couple and continue to move away from each other, e.g., the magnetic force holding the first latching element 118 and the second latching element 120 together is exceeded, or a latching force due to a geometrical fit is exceeded. Then, once decoupled, the first latching element 118 and the second latching element 120 continue to move away from one another according to the further movement of the first rotatable ring 102 and the second rotatable ring 104 back towards the open position.

Thus, the latching elements can be decoupled as a result of movement of the forearm orthogonally or substantially orthogonally a direction associated with the pulling force. In one embodiment, when the first latching element 118 and the second latching element 120 are de-coupled, the apparatus 100 automatically returns to the open position as part of a rotational bias towards the open position. The bias is less than the coupling force when the first latching element 118 and the second latching element 120 are coupled to maintain such coupling. As mentioned, when apparatus 100 is in the closed position, the forearm or elbow can be used to pull against the first pulling element 110 and/or the second pulling element 112, by exerting a force perpendicularly, or generally perpendicularly, outward from the door, and without touching any part of the user's hand.

Figure 3:
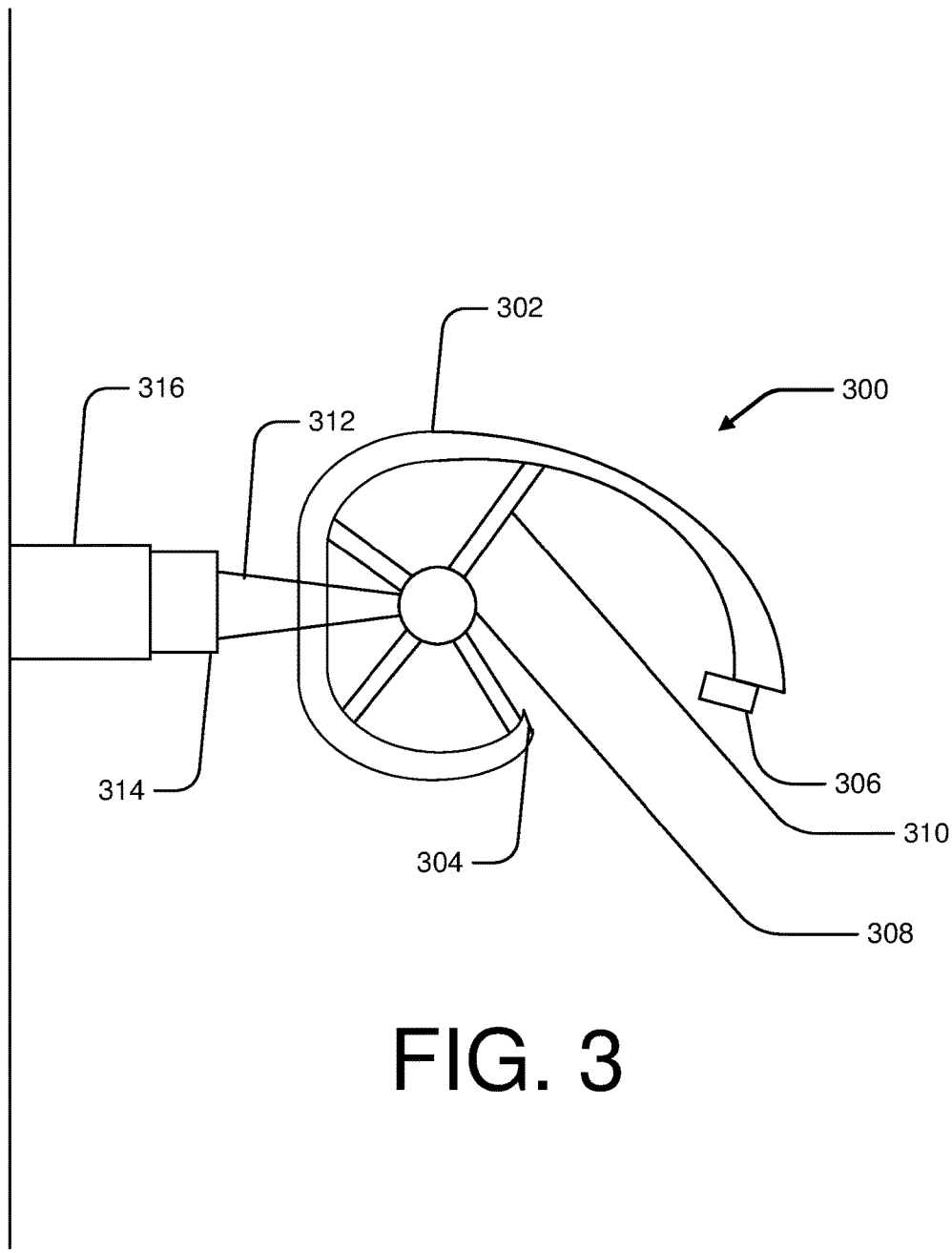
FIG. 3 illustrates an example diagram of a one-ring structure-opening apparatus in the open position.

FIG. 3 illustrates an example, non-limiting apparatus 300 comprising, instead of the first rotatable ring 102 and the second rotatable ring 104 of FIGS. 1-2, a single ring, e.g., rotatable ring 302. FIG. 3 further illustrates a forearm push point 304, a forearm catch element 306, a ring rotation element 308, spokes 310, a supporting frame 312, a door attachment hardware element 314, and a door knob/handle 316. IN this example, the rotatable ring element 302 is unenclosed. Optionally, the ring rotation element 308 is located at the center of the rotatable ring 302 and is connected to the first rotatable ring 302 by spokes 310. The ring rotation element 308 allows the rotatable ring 302 to rotate substantially about its center. The forearm push point is located on the inner cross section (the cross section on the side of the ring opening that is closest to the door or structure) of the rotatable ring 302. The forearm catch element 306 is located on the outer cross section (the cross section on the side of the ring opening that is farthest from the door or structure) of the rotatable ring 302. The supporting frame 312 holds the rotatable ring 302 in a vertical position so that the unenclosed side of the rotatable ring 302 is directed downwards. The supporting frame 312 can be connected to the door attachment hardware element 314. In one embodiment, the supporting frame 312 biases the rotatable ring 302 to the open position in the absence of external force, to enable ease of access for a user to enter or exit their forearm/elbow from the apparatus 300.

Figure 4:
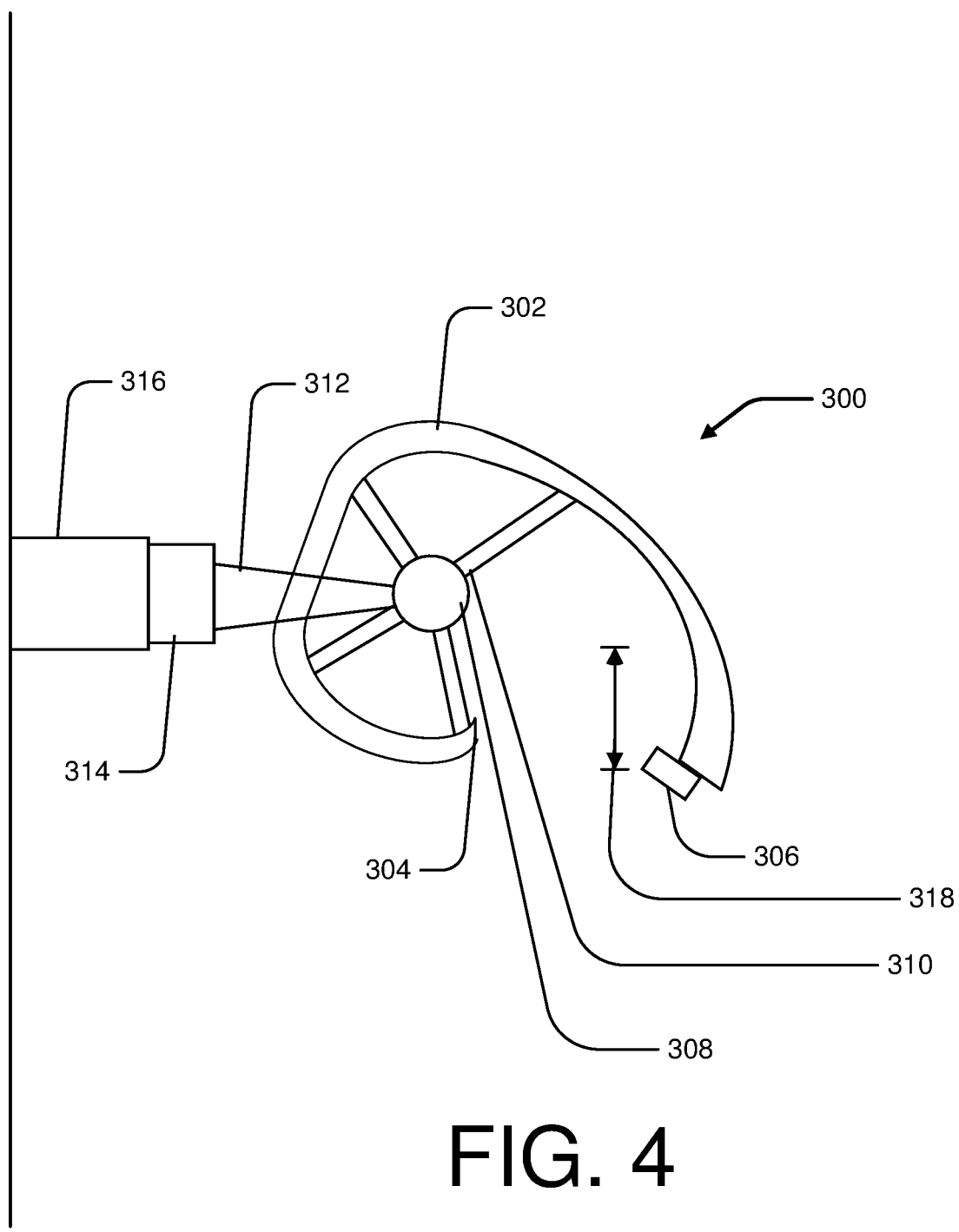
FIG. 4 illustrates an example diagram of a one-ring structure-opening apparatus in the closed position.

FIG. 4 illustrates the apparatus 300 in a 'closed' position, which is the position that facilitates opening or closing of a door, or other structure, with one's forearm/elbow by pulling or pushing therewith and also illustrates the rotatable ring 302, the forearm push point 304, the forearm catch element 306, the ring rotation element 308, the spokes 310, the supporting frame 312, the door attachment hardware element 314, the door knob/handle 316, and the forearm pull region 318. In this regard, a forearm or elbow can push the forearm push point 304 towards the door, causing the rotation of the rotatable ring 302 to the closed position as shown in FIG. 4. Optionally, the apparatus 300 stops in the closed position, at least temporarily, and/or as a result of mechanical means in an extended position. As the rotatable ring 302 rotates, the forearm catch element 306 lowers so that a forearm/elbow can pull against the forearm catch element 306 perpendicularly outward from the door.

Figure 5:
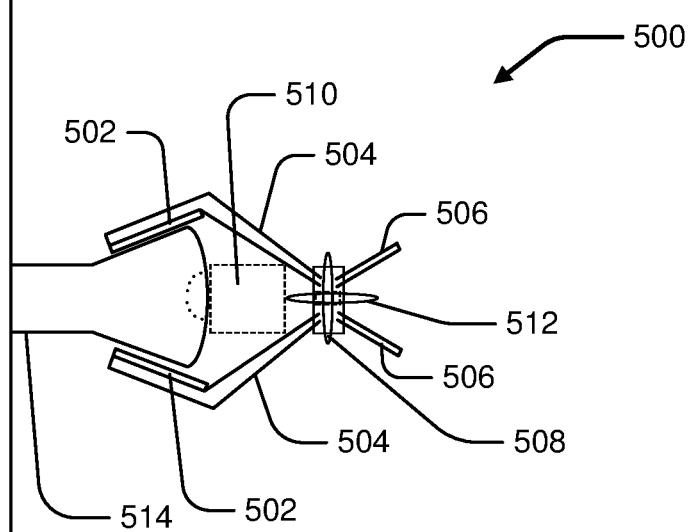
FIG. 5 illustrates an example diagram of a rotatable clamping apparatus.

FIG. 5 illustrates another example, non-limiting door attachment apparatus 500, which comprises a gripping element 502, a clamping element 504, clamping element squeeze handles 506, clamping element attachment structure 508, a space for key 510, a rotation plane converter 512, and a door knob 514. The clamping squeeze handles 506 open and close the clamping element 504. The clamping element 504 surrounds the door knob 514 or door handle. The gripping element 502 is located on the clamping element 504 and is configured to grip the door knob 514 or door handle firmly enough so that the apparatus 500 can facilitate the turning of the door knob 514 or handle, while permitting entry of a key. In this way, the locking and unlocking of the door knob 514 is separated from the opening and closing of the door using the apparatus 500 without use of hands.

In this regard, the rotation plane converter 512 of apparatus 500 converts a first plane of rotation of the first rotatable ring 102 and the second rotatable ring 104 (or rotatable ring 302) to a second plane of rotation of the clamping element that causes a rotation of the rotatable doorknob to open the door. The rotation plane converter 512 can comprise a first gear that rotates substantially in the first plane of rotation and a second gear that rotates substantially in the second plane of rotation, and wherein first rotation of the first gear in the first plane of rotation cooperatively engages with the second gear to cause second rotation of the second gear in the second plane of rotation. For one non-limiting example, the first plane of rotation can be substantially orthogonal to the second plane of rotation. For another non-limiting example, the first plane of rotation can be substantially parallel to the second plane of rotation (see, e.g., FIGS. 6-7).

Figure 6:
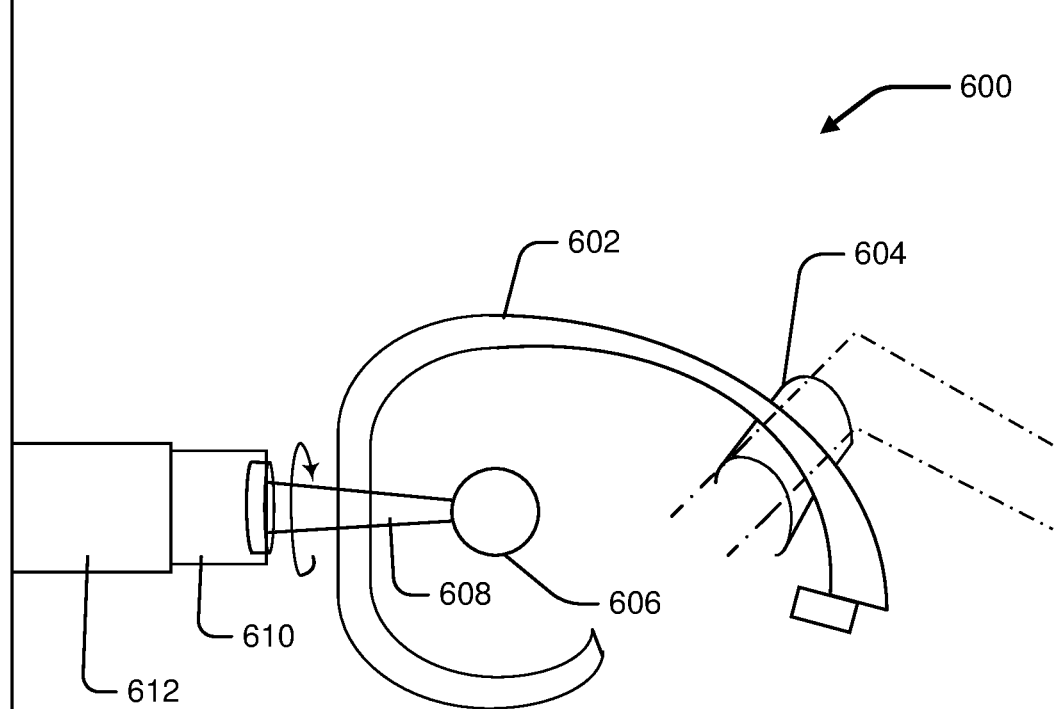
FIG. 6 illustrates an example diagram of a vertically oriented rotatable one-ring structure opening apparatus.

FIG. 6 illustrates another example, non-limiting apparatus 600, which comprises comprising a rotatable ring 602, a forearm receiver 604, a fixed rotation element 606, a supporting frame 608, a door attachment hardware element 610, and a door knob/handle 612. In the example, the rotatable ring 602 is unenclosed with the ring opening directed downwards. FIG. 6 illustrates apparatus 600 in the unrotated position. In this regard, the forearm receiver 604 facilitates reception of the user's forearm, so that the user may begin to rotate the door knob/handle 612 via the apparatus 600, via pivot of the elbow and/or rotation of the shoulder. When the user's forearm is received by forearm receiver 604, by turning a user's arm parallel to the plane of rotation of the door knob/handle 612, the rotation of the user's arm is transferred via the apparatus 600 to also rotate the door knob/handle 612.

Figure 7:
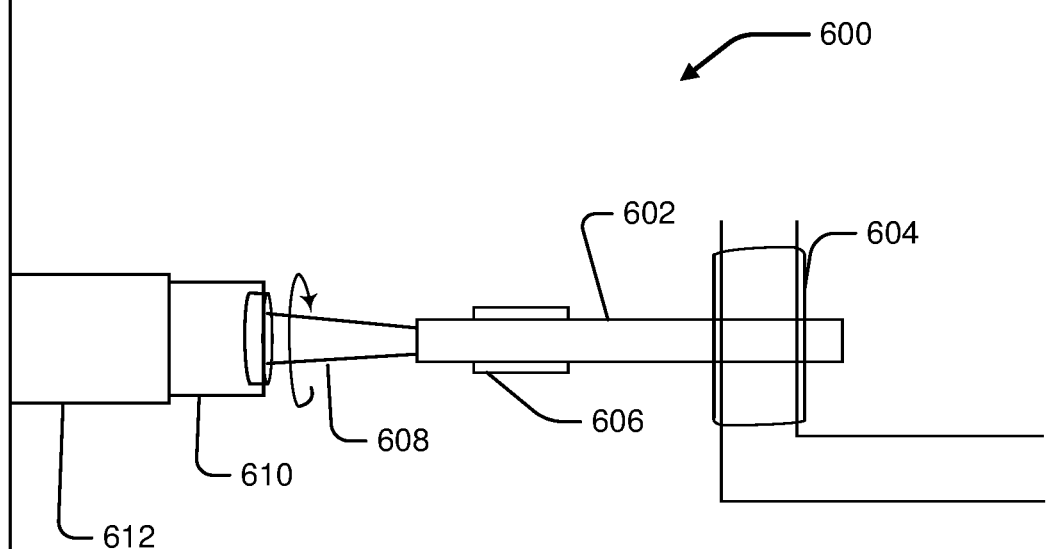
FIG. 7 illustrates an example diagram of a horizontally oriented rotatable one-ring structure-opening apparatus.

In this regard, FIG. 7 illustrates apparatus 600 in the rotated position, with like elements with like labels. The fixed rotation element 606 allows the rotatable ring 602 to rotate about an axis that is perpendicular to a surface of a door to which the apparatus 600 is attached via the door attachment hardware element 610, the axis defining the first plane of rotation that intersects a center or near the center of the rotatable doorknob/handle 612. As shown, the user's forearm has been rotated from horizontal with the floor (not shown, assumes floor is perpendicular to the door) to being perpendicular to the floor, or pointed at the ceiling (not shown). As a result, the door attachment hardware element 610 has correspondingly rotated, in the second plane of rotation parallel with the surface of the door, in cooperation with the rotatable ring element 602 to cause the rotation of the rotatable doorknob/handle 612 to open the door, without touching the door knob/handle 612 with the user's hand.

Figure 8:
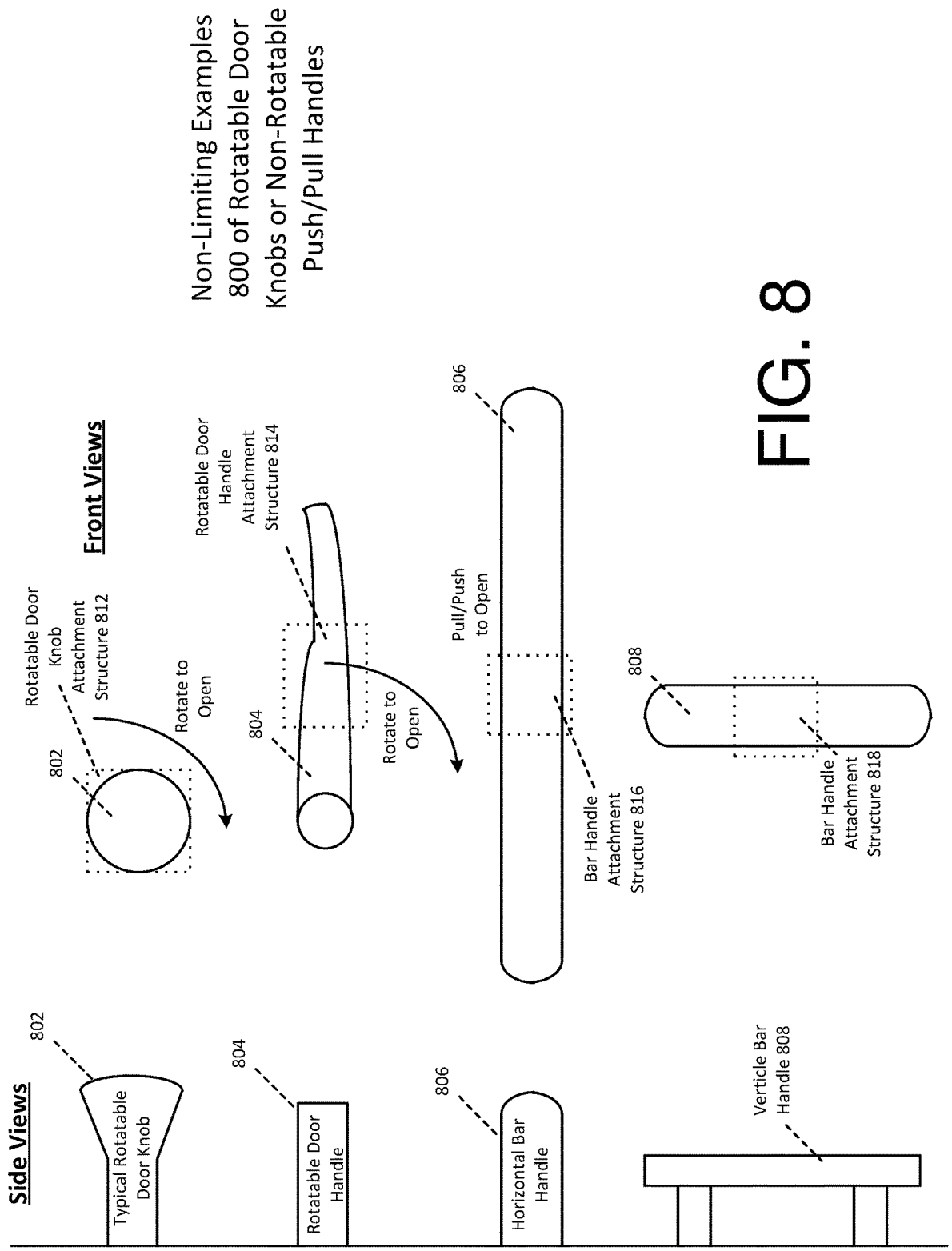
FIG. 8 presents an example, non-limiting, diagram of types of doorknobs and door handles to which a structure-opening apparatus could be attached.

FIG. 8 presents an example, non-limiting, diagram of types or examples 800 of doorknobs and door handles or doorknobs that can be employed for one or more door knob/handles (e.g., 130, 316, 514, and 612) in accordance with various aspects and embodiments of the disclosed subject matter. It is to be appreciated and understood that the door attachment hardware element (e.g., 128, 314, 500, and 610) can be customized to be in any suitable shape and any suitable size in accordance with various aspects and embodiments of the disclosed subject matter. For instance, as examples, a typical rotatable door knob 802, a rotatable door handle 804, a horizontal bar handle 806, and a vertical bar handle 808, are shown from both side views, and front views. The typical rotatable door knob 802, the handle rotatable door knob 804, the horizontal bar handle 806, and the vertical bar handle 808 can have respective door attachment elements, including rotatable door knob attachment structure 812, rotatable door handle attachment structure 814, bar handle attachment structure 816, and bar handle attachment structure 818, respectively.

Figure 9:
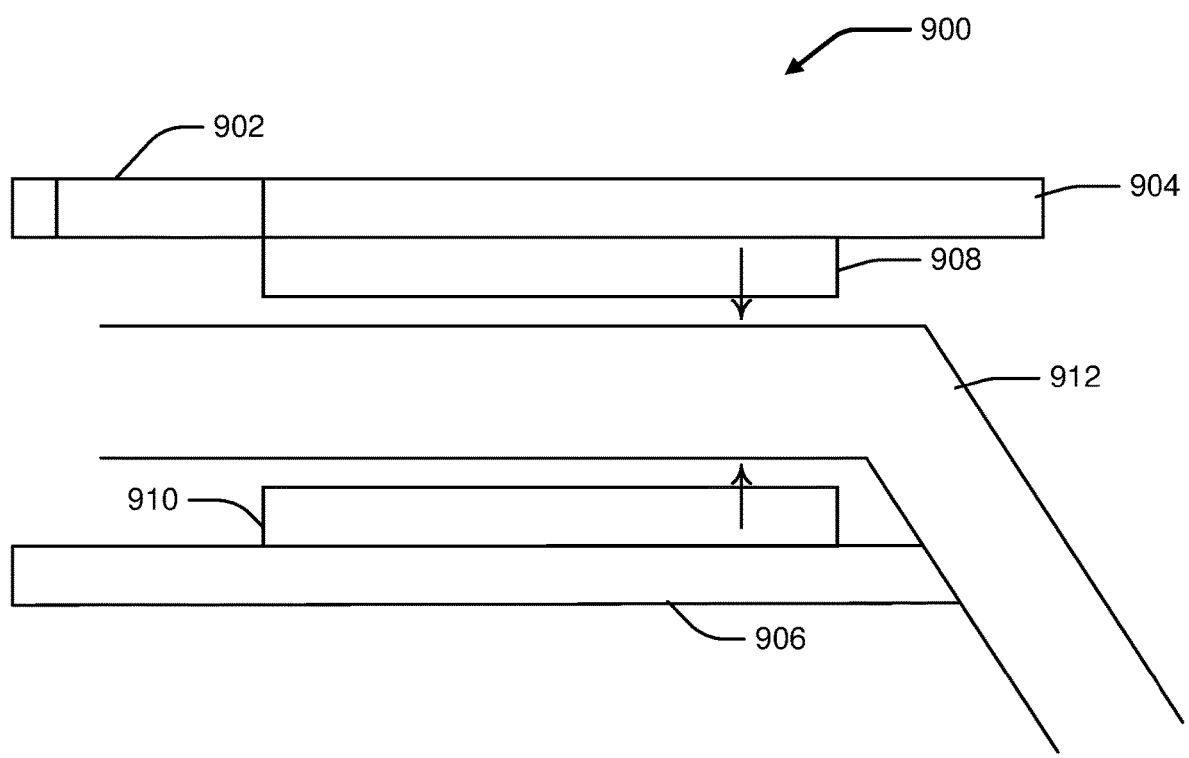
FIG. 9 illustrates an example diagram of a forearm grip structure-opening apparatus in an open position.

FIG. 9 illustrates an example, non-limiting apparatus 900 in an open position comprising a motion sensor component 902, an upper housing plank 904, a lower housing plank 906, a first grip element 908, a second grip element 910, and an arm 912. The motion sensor component 902, when activated by motion determined to be threshold likely to be a user's forearm, activates respective actuators (not shown as being inside the upper housing plank 904 and the lower housing plank 906, respectively) to move the first grip element 908 and the second grip element 910 towards each other. Also, in one embodiment, optionally, only one of the first grip element 908 or the second grip element 910 need to be moved by an actuator since the movable one motivated by the actuator can move to meet the static one (with the forearm between). Further, a resistance sensor (not shown as being inside at least one of the upper housing plank 904 or the lower housing plank 906) that detects pressure against at least one of the first grip element 908 or the second grip element 910 can also be included, so as to maintain a safe amount of pressure against a user's arm, by enforcing operation within a threshold pressure.

The first grip element 908 is movably coupled to the upper housing plank 904 and the second grip element 910 is movably coupled to the lower housing plank 906. The long side of the upper housing plank 904 can be secured to a door and the long side of the lower housing plank 906 can also be secured to the same door. As shown in this example, the first grip element 908 and the second grip element 910 are positioned so that the first grip element 908 and the second grip element 910 are facing each other. In the open or default position, as shown in FIG. 9, there is enough room between the first grip element 908 and the second grip element 910 for a person's forearm to fit between the first grip element 908 and the second grip element 910.

The first grip element 908 can be angled so that a first width of the first grip element 908 is thinner at a first position closer to the door than a second width of the first grip element 908 at a second position farther from the door. Similarly, the second grip element 910 can be angled so that a third width of the second grip element 910 is thinner at a third position closer to the door than a fourth width of the second grip element 910 at a fourth position farther from the door. This is shown best in the cross-sectional view of FIG. 10B described below when the apparatus 900 is in the closed position.

Figure 10A:
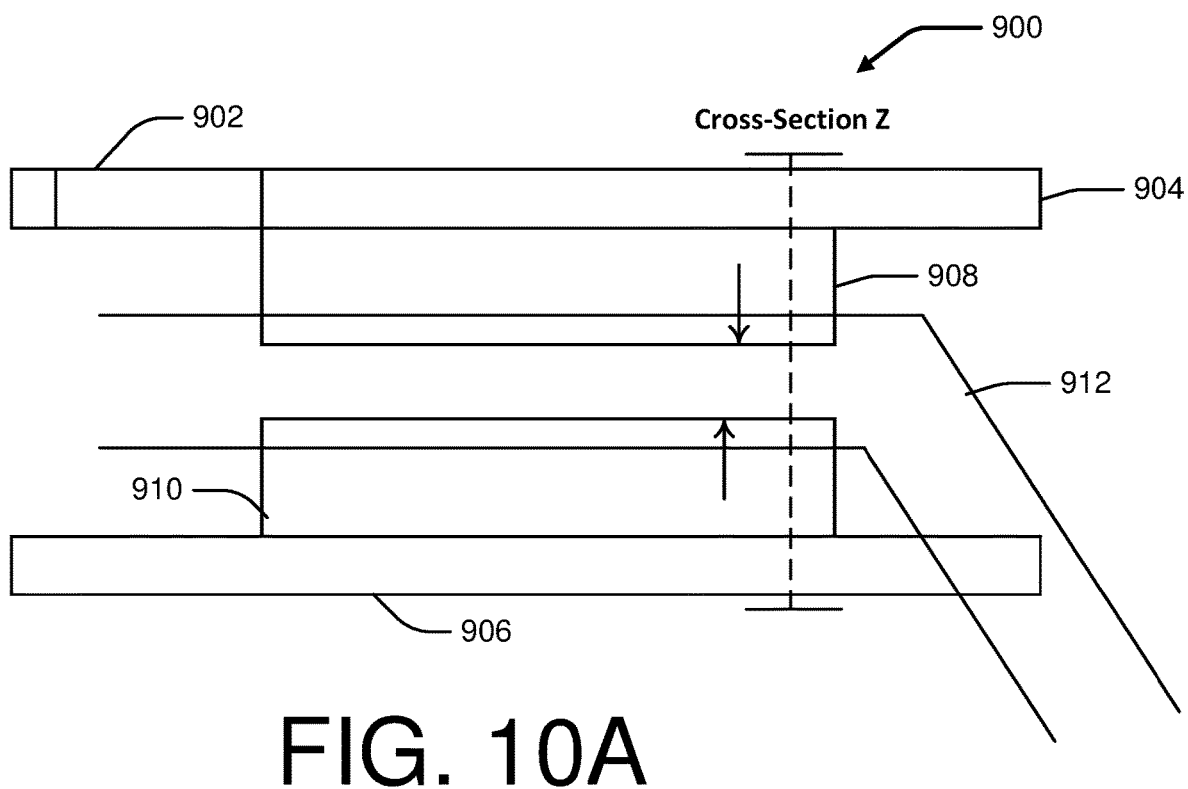
FIG. 10A illustrates an example diagram of a forearm grip structure-opening apparatus in a closed position.

FIG. 10A illustrates apparatus 900 in the closed position. The motion sensor 902 can detect the presence of an object in a defined space which includes the space between the first grip element 908 and the second grip element 910. When an object (e.g., a forearm) is detected between the first grip element 908 and the second grip element 910, the motion sensor cues the actuator to move the first grip element 908 towards the second grip element 910 so that the object (forearm) is secure and a person can pull a door open. In one embodiment, an image processor is able to distinguish between motion of an object that is threshold likely to be a forearm, and motion that is not threshold likely to be a forearm.

As mentioned, the resistance sensor can be located inside the first grip element 908 or the second grip element 910. When the resistance sensor detects a defined amount of pressure against at least one of the first grip element 908 or the second grip element 910, the resistance sensor cues the actuator(s) to cease the movement of the first grip element 908 and/or the second grip element 910 towards each other. After a defined amount of time from the presence of the object being detected by the motion sensor component 902, the actuator moves the first grip element 908 and the second grip element 910 away from each other back to the open or default position of FIG. 9. Alternatively, voice command logic such as "door engage" or "door release" can be built into the actuator intelligence to actuate or return to the open position, respectively.

Figure 10B:
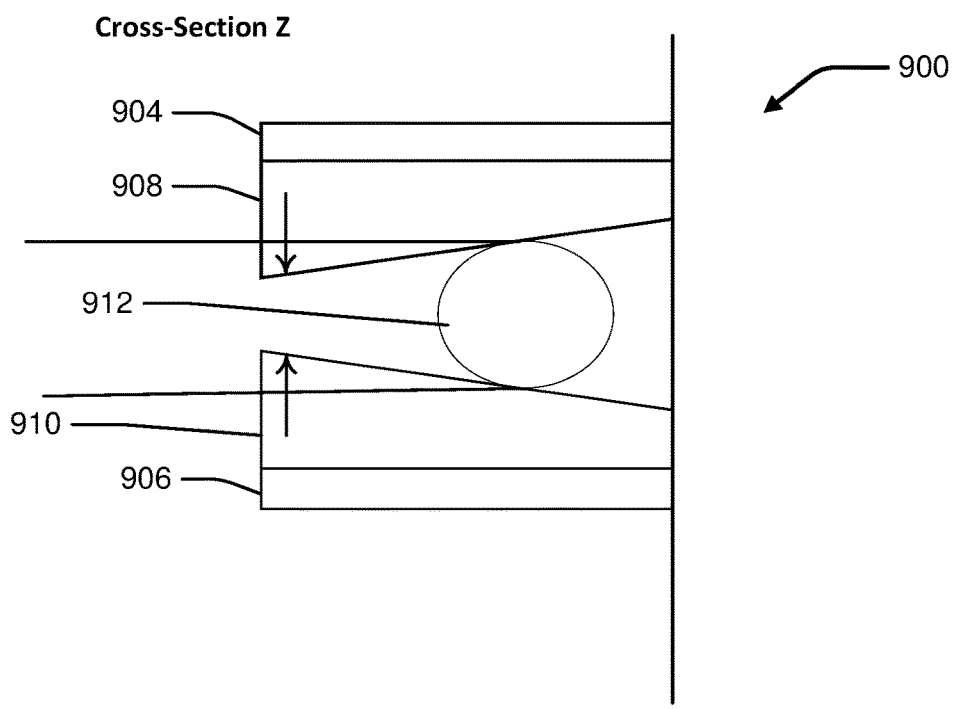
FIG. 10B illustrates an example diagram of the cross section a forearm grip structure-opening apparatus in a closed position.

FIG. 10B represents a cross section view of the apparatus 900, to show the angling of the first grip element 908 and the second grip element 910 to form a 'trap' of the forearm in the closed position, in order to enable the forearm to pull against the first grip element 908 and the second grip element 910 to open or shut a door as the configuration of the door may be.

Figure 11A:
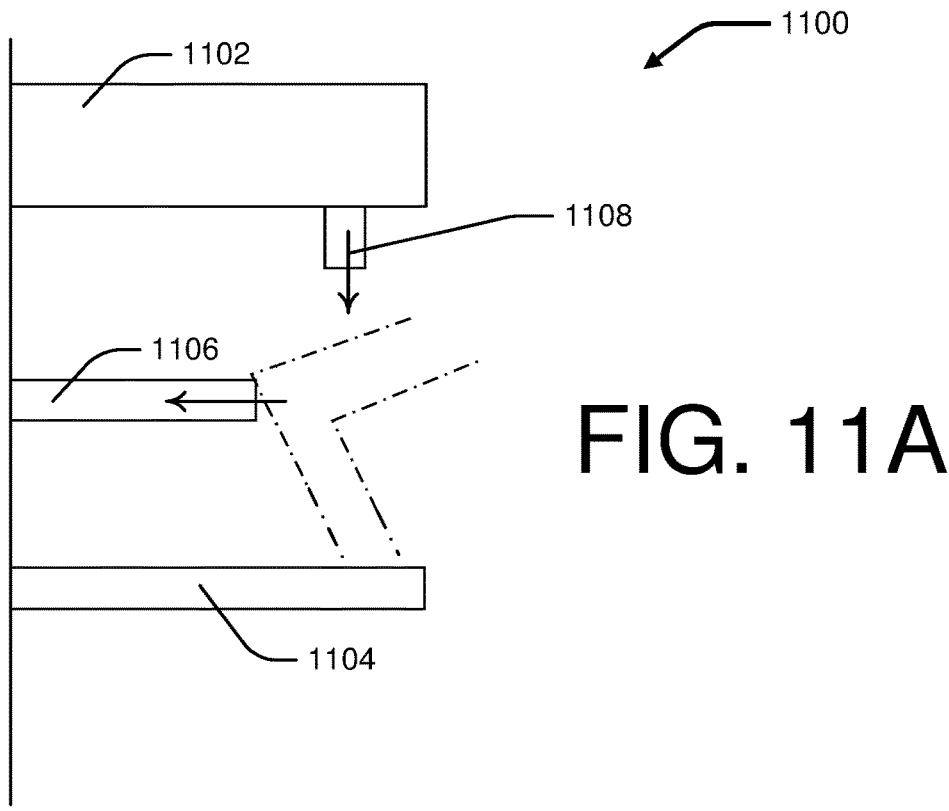
FIG. 11A illustrates an example diagram of a structure-opening apparatus comprising a lowering/rising vertical bar in the raised position.

FIG. 11A illustrates an example, non-limiting apparatus 1100 in an open position comprising an upper housing element 1102, a lower housing element 1104, a horizontal pushing element 1106, and a vertical pulling element 1108. The horizontal pushing element 1106 protrudes perpendicularly, or substantially perpendicularly, from the door and is configured to be pushed towards the door. The horizontal pushing element is electronically coupled to the vertical pulling element 1108. The vertical pulling element 1108 is recessed at least partly in the upper housing element 1102 in a recessed position and can move from the recessed position towards the lower housing element 1104 to an extended position in response to the horizontal pushing element 1106 being pushed by a forearm or elbow (user arm shown in dashed line) at least a first threshold amount, and that returns the pulling element to the recessed position in response to the horizontal pushing element 1106 being pushed at least a second threshold amount greater than the first threshold amount.

Figure 11B:
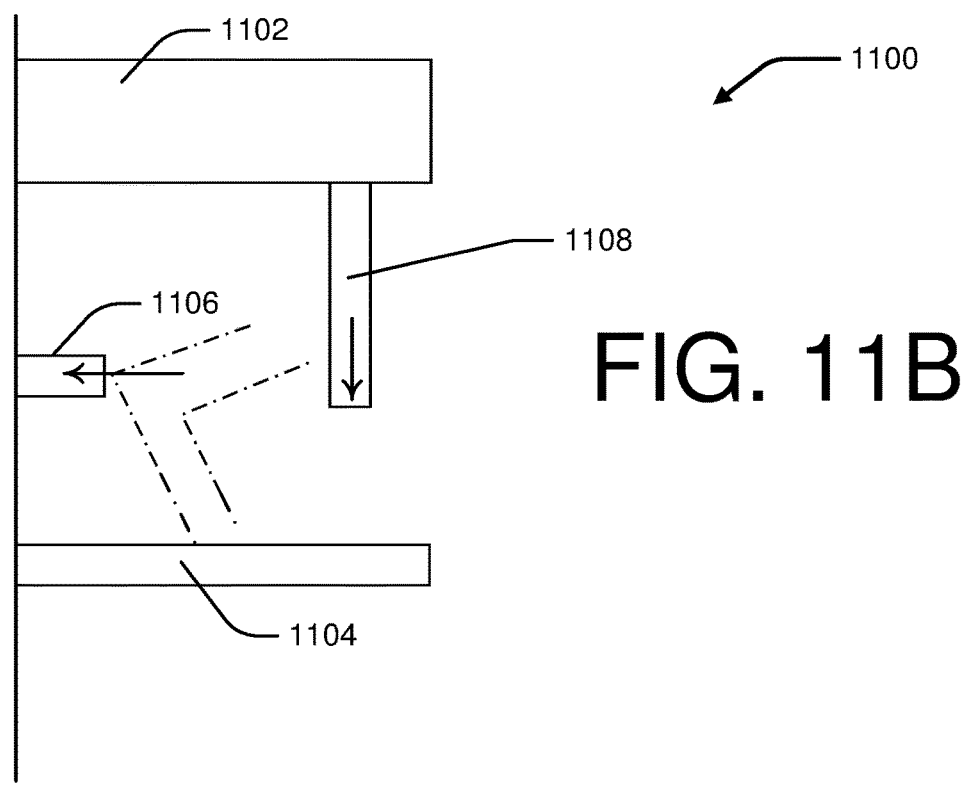
FIG. 11B illustrates an example diagram of a structure-opening apparatus where an elbow is pushing in the horizontal pushing bar to a first push point to lower the vertical bar.

FIG. 11B illustrates the apparatus 1100 where the horizontal pushing element 1106 has been pushed to the first threshold amount, thereby causing the vertical pulling element 1108 to extend into the space between the upper housing element 1102 and the lower housing element 1104, according to the directions of the respective arrows, as shown.

FIG. 12A illustrates the apparatus 1100 in the closed position, whereby a user's elbow or forearm is usable to pull against the vertical pulling element 1108 to open or close a door as the case may be.

FIG. 12B illustrates the apparatus 1100 where the horizontal pushing element 1106 has been pushed to the second threshold amount, thereby causing the vertical pulling element 1108 to recede into the upper housing element 1102. It is noted that the upper housing element 1102 and the lower housing element 1104 can be flipped in the subject embodiment, e.g., the lower housing element 1104 can include the vertical pulling element 1108 instead.

Figure 13A:
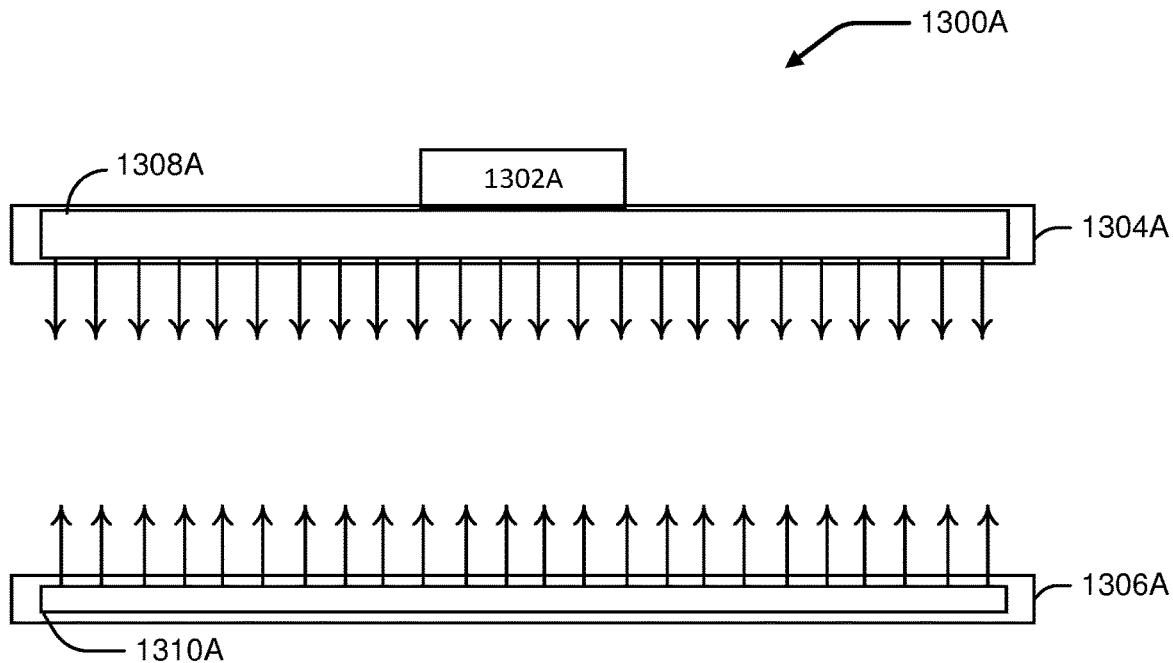
FIG. 13A illustrates an example diagram of a motion sensor and ultraviolet light and/or heat emitting elements.

FIG. 13A illustrates an apparatus 1300A comprising a motion sensor component 1302A, an upper housing element 1304A, a lower housing element 1306A, an upper ultraviolet light emitting component 1308A, and a lower ultraviolet light emitting component 1310A. The apparatus 1300A can also include a timer, which is not shown, or otherwise incorporated into the circuitry associated with the motion sensor component 1302A, the upper ultraviolet light emitting component 1308A, or the lower ultraviolet light emitting component 1310A of the apparatus 1300A. In one embodiment, the apparatus 1300A can be implemented in conjunction with the apparatuses 100 and 300. In this regard, the motion sensor component 1302A can detect when the apparatus 1300A moves to an open position from a closed position, or the actuator(s) can signal when this has occurred. When this occurs, the motion sensor component 1302A component or actuator(s) or other intelligence can cue the timer to start. When the timer reaches a defined time and no motion has been detected in the meantime, the timer component cues the ultraviolet lights 1308A and 1310A to direct ultraviolet light (or any specified wavelength ranges that are desirable for eradicating microbes) towards the rotatable ring 302 or the first and second rotatable rings 102 and 104 until a defined time limit is reached, or until motion is detected, whichever occurs first. This way, microbes can be eradicated after each use, without irradiating a user with the ultraviolet light, since, if the irradiation is interrupted by motion, it is stopped.

Figure 13B:
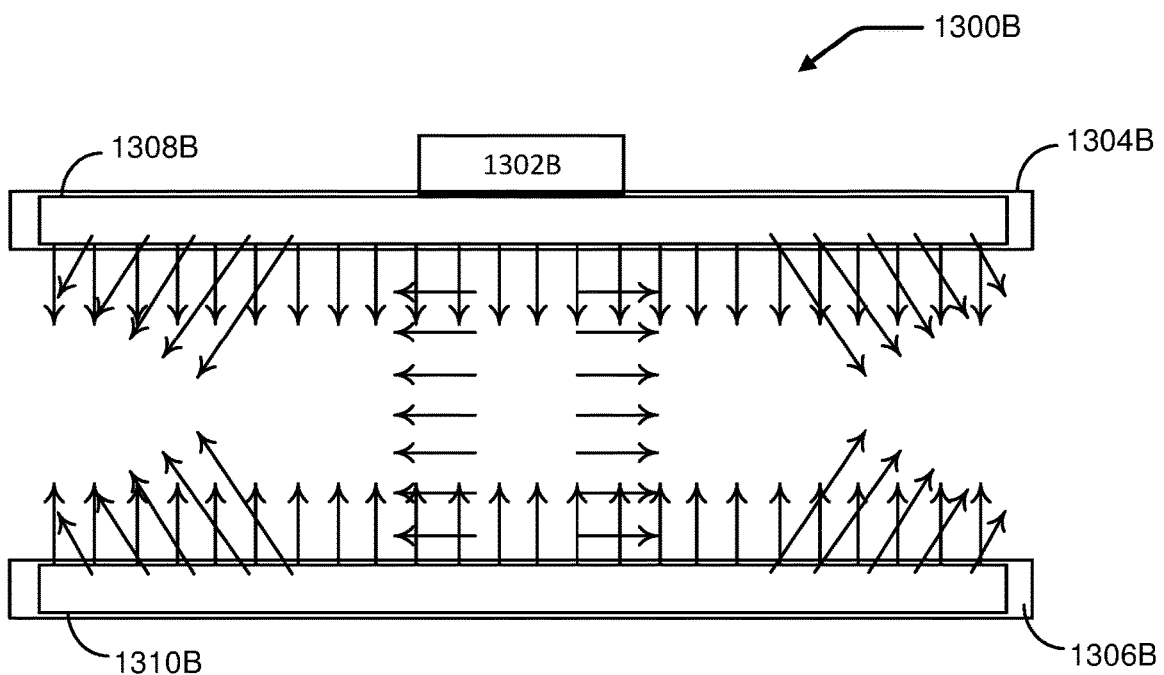
FIG. 13B illustrates an example diagram of a motion sensor and wind producing elements.

Similar to, or combinable with FIG. 13A, FIG. 13B illustrates an example, non-limiting apparatus 1300B comprising a motion sensor component 1302B, an upper housing element 1304B, a lower housing element 1306B, an upper wind producing component 1308B, and a lower wind producing component 1310B. The apparatus could also include a timer which is not shown, similar to FIG. 13A. In one embodiment, the apparatus 1300B can be implemented in conjunction with the apparatuses 100 and 300. The motion sensor component 1302B can detect when the apparatus moves to an open position from a closed position, or as mentioned, the actuator(s) can signal the fact. When this occurs, the timer can be cued to start. When the timer reaches a defined time and no further motion has been detected, the timer component cues the wind producing elements 1308B and 1310B to direct wind towards the rotatable ring 302 or the first and second rotatable rings 102 and 104 for a defined amount of time, to facilitate evaporation of any liquids or droplets that may otherwise aid a microbe's life, in order to minimize risk of exposure to any such microbes.

Apparatuses 1300A and 1300B could also be implemented in conjunction with, or otherwise combined with, apparatuses 100, 300, and 600.

Apparatuses 1300A and 1300B could also be implemented in conjunction with apparatus 900, wherein the motion sensors 1302A, 1302B and 902 are the same motion sensor and the timer cues the ultraviolet light emoting element 1308A and the wind producing component 1308B to be directed at the first gripping element 908 and the second gripping element 910 after the motion sensor 902 ceases to detect an object in the defined space for a defined amount of time.

Apparatuses 1300A and 1300B could also be implemented in conjunction with apparatus 1100 wherein the timer cues the ultraviolet light emoting element 1308A and the wind producing component 1308B to be directed at the horizontal pushing element 1106 and the vertical pulling element 1108 the apparatus has been in the open position for a defined amount of time.

Figure 14:
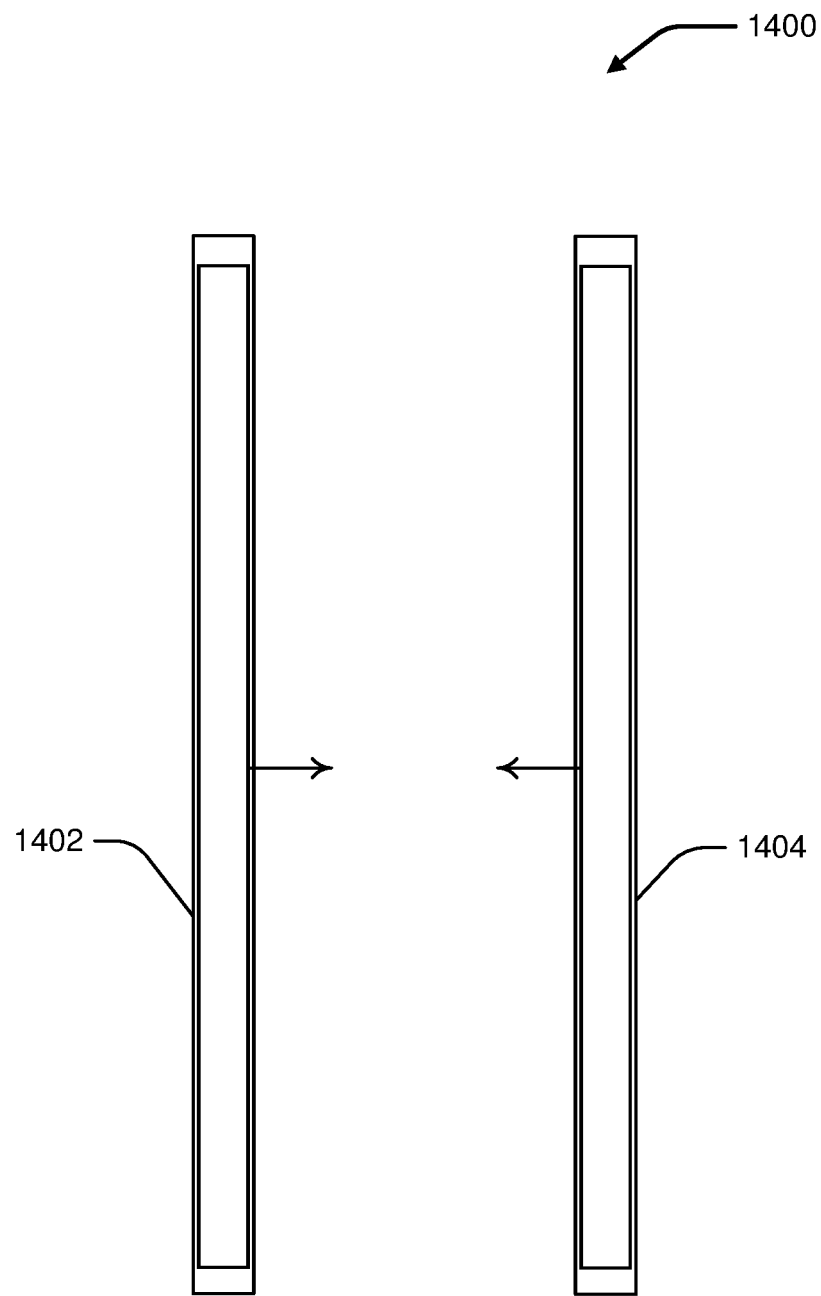
FIG. 14 illustrates an example diagram of right and left side housings.

FIG. 14 illustrates an example, non-limiting apparatus 1400 comprising a left housing element 1402 and a right housing element 1404. This apparatus 1400 demonstrates that any of the embodiments described herein with respect to an upper housing element and a lower housing element could also be described as a left (or right) housing element 1402 and a right (or left) housing element 1404, respectively, in another embodiment where a knee or calf replaces an elbow or forearm by a 90 degree rotation of the given apparatus for the elbow or forearm, as described hereinabove.

Figure 15:
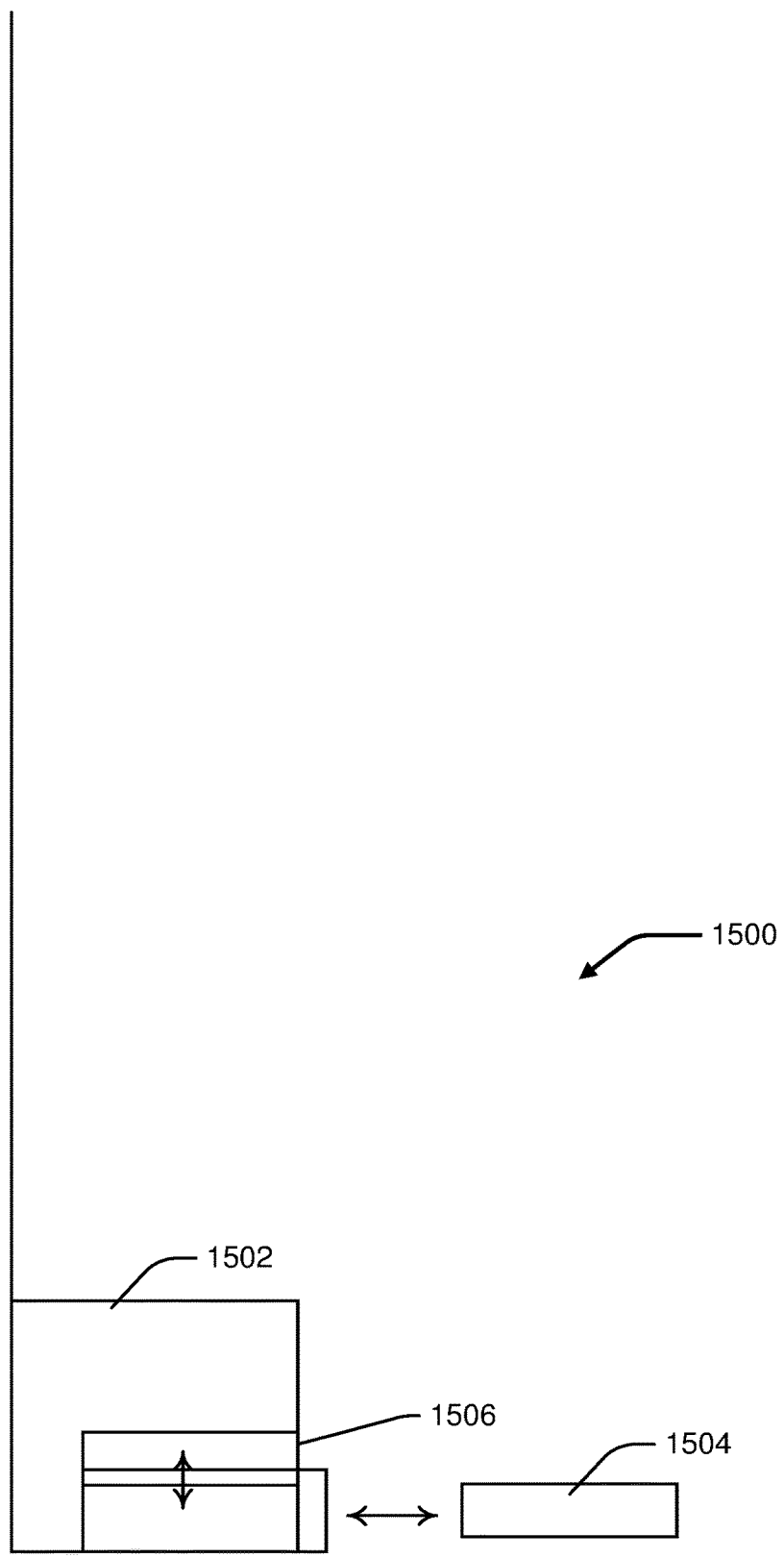
FIG. 15 illustrates an example diagram of a shoe-squeeze engage structure.

FIG. 15 illustrates another example, non-limiting apparatus 1500 that facilitates the opening and closing of a door without implicating touching a user's hand, comprising a housing element 1502, a foot/shoe/sock engage structure 1504, and a foot/shoe/sock exit/entry opening 1506. The apparatus 1500 can also comprise a motion sensor that is not shown and an actuator that is not shown, as in other embodiments described above. The housing element 1502 is secured to a door and encompasses the foot/shoe/sock engage structure 1504. The foot/shoe/sock exit/entry opening 1506 is an opening in the foot/shoe/sock engage structure 1504. A motion sensor can detect the presence of an object (foot/shoe/sock) in the foot/shoe/sock exit/entry opening 1506. The motion sensor cues the actuator to engage the foot/shoe/sock so that a door can be pulled or pushed open. Similarly, as described herein elsewhere, pressure sensor(s) can be used to limit an amount of pressure exerted on a foot/shoe to a safe amount of pressure. Once a user's foot/sock/shoe, etc. enters the opening 1506 on the housing 1502 at the bottom of the door, a lifting of the foot engages enables the user to push or pull on the door with their leg/foot by electromechanical operation or by squeezing of the foot. Conversely, lowering the foot disengages the squeezing, enabling the user to remove the foot through the opening 1506.

It is also worth noting that any circuitry provided with any of the foregoing embodiments that enable motion detection, timing, wind generation, light irradiation, actuation, storage or other functionality described herein, can be paired with an application ("app") or web site access to communicate information about, or receive commands instructing, the given apparatus. For instance, as an independent app or as part of an electronic door locking service, and corresponding user interface, information about the state of a given opening/closing apparatus described herein can also be reported, and commands to control the apparatus can be received via the user interface.

What has been described above includes examples of apparatuses, systems and corresponding methods illustrative of the disclosed subject matter. It is, of course, not possible to describe every combination of components or methods herein. One of ordinary skill in the art may recognize that many further combinations and permutations of the disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

In addition to the various implementations described herein, it is to be understood that other similar implementations can be used or modifications and additions can be made to the described implementation(s) for performing the same or equivalent function of the corresponding implementation(s) without deviating therefrom. Still further, multiple processing chips or multiple devices can share the performance of one or more functions described herein where circuitry is described explicitly or implicitly. Accordingly, the description is not to be limited to any single implementation, but rather is to be construed in breadth, spirit and scope in accordance with the appended claims.

What is claimed is:

1. An apparatus, comprising:
   a first rotatable ring, wherein the first rotatable ring is not enclosed and has an opening configured to receive a forearm,
   a first push surface located on an inner cross section of the first rotatable ring adjacent to the opening of the first rotatable ring, the first push surface configured to receive a pushing force from the forearm to open or close a door,
   a first pull surface located on an outer cross section of the first rotatable ring adjacent to the opening of the first rotatable ring, the first pull surface being configured to receive a pulling force from the forearm to open or close the door,
   a forearm catch attached to the first pull surface that is configured to receive and stabilize the pulling force from the forearm, in connection with reception of the pulling force on the first pull surface,
   a first ring rotation element that is attached to the first rotatable ring and enables the first rotatable ring to rotate between an open position associated with reception of the pushing force via the forearm through the opening against the first push surface and a closed position associated with the pulling force via the forearm against the first pull surface,
   a supporting frame that biases the first rotatable ring in the open position when there is no external force applied to the first push surface, and
   door attachment hardware that secures the apparatus to a door opening structure of the door.

2. The apparatus of claim 1, wherein the forearm catch is part of the first pull surface.

3. The apparatus of claim 1, wherein the opening is a first opening, wherein the outer cross section of the first rotatable ring is a first outer cross section, wherein the inner cross section of the first rotatable ring is a first inner cross section, and further comprising:
   a second rotatable ring, located adjacent to the first rotatable ring, wherein the second rotatable ring is not enclosed and has a second opening,
   a second push surface located on the second inner cross section of the second rotatable ring adjacent to the second opening of the second rotatable ring, the second push surface configured to further receive the pushing force from the forearm to open or close the door,
   a second pull surface located on the second outer cross section of the second rotatable ring adjacent to the second opening of the second rotatable ring, the second pull surface being configured to receive the pulling force from the forearm to open or close the door,
   a second ring rotation element that is attached to the second rotatable ring and enables the second rotatable ring to rotate between the open position associated with reception of the pushing force via the forearm through the opening against the first push surface and the second push surface and the closed position associated with the pulling force via the forearm against the first pull surface and the second pull surface, and
   a latching element, comprising
      a first coupling element, configured to couple with a second coupling element, located on the first outer cross section of the first rotatable ring adjacent to the first opening of the first rotatable ring,
      the second coupling element, configured to couple with the first coupling element, located on a second outer cross section of the second rotatable ring adjacent to the second opening of the second rotatable ring,
   wherein the latching element enables coupling, according to the closed position, of the first rotatable ring and the second rotatable ring when the first coupling element and the second coupling element come into contact with one another, and enables decoupling, according to the open position, of the first rotatable ring and the second rotatable ring when the first coupling element and the second coupling element are moved away from one another, and
   wherein the supporting frame biases the first rotatable ring and the second rotatable ring in the open position when there is no external force applied to the first push surface or the second push and when the first rotatable ring and the second rotatable ring have been decoupled.

4. The apparatus of claim 3, further comprising:
a sensor configured to detect when the first rotatable ring and the second rotatable ring are rotated into the open position from the closed position,
a timer that begins counting when the first rotatable ring and the second rotatable ring are rotated into the open position from the closed position, and
a wind generator configured to direct air flow onto the first rotatable ring and the second rotatable ring when the timer reaches a defined length of time, to facilitate evaporation of any liquid within the air flow.

5. The apparatus of claim 3, further comprising:
a first sensor configured to detect when the first rotatable ring and the second rotatable ring are rotated into the open position from the closed position,
a second sensor configured to detect motion within a defined proximity of the apparatus,
a timer that begins counting when the first rotatable ring and the second rotatable ring are rotated into the open position from the closed position, and
an ultraviolet light source configured to radiate ultraviolet light on the first rotatable ring and the second rotatable ring in response to the timer reaching a defined length of time and in response to no motion having been detected by the second sensor within the defined proximity for at least a most recent part of the defined length of time.

6. The apparatus of claim 3, wherein the first coupling element and the second coupling element of the latching element couple by magnetic force of respective magnets of the first coupling element and the second coupling element in the closed position.

7. The apparatus of claim 3, wherein the first coupling element and the second coupling element of the latching element couple by mating of matching geometries of the first coupling element and the second coupling element that press fit against one another in the closed position.

8. The apparatus of claim 3, wherein the coupling of coupling elements comprises at least one of coupling the coupling elements by magnetic force or via mating of matching geometries of the coupling elements that press fit against one another in the open position, and wherein the coupling of the coupling elements is decoupled as a result of movement of the forearm orthogonally or substantially orthogonally a direction associated with the pulling force.

9. The apparatus of claim 3, wherein the door attachment hardware comprises:
a clamping element that clamps onto a rotatable doorknob,
a gripping contact surface on the clamping element that enables the clamping element to increase a grip on the rotatable doorknob by the clamping element relative to without the gripping contact surface, and
a rotation plane converter that converts a first plane of rotation of the first rotatable ring and the second rotatable ring to a second plane of rotation of the clamping element that causes a rotation of the rotatable doorknob to open the door.

10. The apparatus of claim 9, wherein the rotation plane converter comprises a first gear that rotates substantially in the first plane of rotation and a second gear that rotates substantially in the second plane of rotation, and wherein first rotation of the first gear in the first plane of rotation cooperatively engages with the second gear to cause second rotation of the second gear in the second plane of rotation.

11. The apparatus of claim 9, wherein:
the first ring rotation element enables the first rotatable ring to rotate about an axis that is perpendicular to a surface of a door to which the apparatus is attached via the door attachment hardware, the axis defining the first plane of rotation that intersects a center or near the center of the rotatable doorknob, and
the door attachment hardware rotates, in the second plane of rotation parallel with the surface of the door, in cooperation with the first rotatable ring element to cause the rotation of the rotatable doorknob to open the door.

12. The apparatus of claim 1, further comprising:
a first sensor configured to detect when the first rotatable ring is rotated into the open position from the closed position,
a second sensor configured to detect motion within a defined proximity of the apparatus,
a timer that begins counting when the first rotatable ring is rotated into the open position from the closed position, and
an ultraviolet light source configured to radiate ultraviolet light on the first rotatable ring in response to the timer reaching a defined length of time and in response to no motion within the defined proximity having been detected by the second sensor for at least a most recent part of the defined length of time.

13. The apparatus of claim 1, further comprising:
a sensor configured to detect when the first rotatable ring is rotated into the open position from the closed position,
a timer that begins counting when the first rotatable ring is rotated into the open position from the closed position, and
a wind generator configured to direct air flow onto the first rotatable ring when the timer reaches a defined length of time, to facilitate evaporation of any liquid within the air flow.

* * * * *